United States Patent [19]

Hagen et al.

[11] Patent Number: 5,026,917
[45] Date of Patent: Jun. 25, 1991

[54] PREPARATION OF 2-ACYL-6-METHYLNAPHTHALENES

[75] Inventors: Gary P. Hagen, Chicago; Gregory E. Schmidt, Batavia; John M. Weis; Thomas G. Smith, both of Naperville, all of Ill.

[73] Assignee: Amoco Corporation, Chicago, Ill.

[21] Appl. No.: 486,783

[22] Filed: Mar. 1, 1990

[51] Int. Cl.$^5$ .............................................. C07C 45/45
[52] U.S. Cl. ..................................... 568/323; 568/324
[58] Field of Search ....................... 568/319, 323, 324

[56] References Cited

U.S. PATENT DOCUMENTS

| | | | |
|---|---|---|---|
| 4,593,125 | 6/1986 | Davenport et al. | 568/322 |
| 4,814,508 | 3/1989 | Gors et al. | 568/323 |
| 4,868,338 | 9/1989 | Magni et al. | 568/322 |
| 4,898,983 | 2/1990 | Towle | 568/323 |

FOREIGN PATENT DOCUMENTS 61-65837  4/1986  Japan ................................. 568/324

*Primary Examiner*—James H. Reamer
*Attorney, Agent, or Firm*—Thomas E. Nemo; William H. Magidson; Ralph C. Medhurst

[57] ABSTRACT

A regioselective acetylation process is provided for converting a 2-methylnaphthalene compound to a 2-acetyl-6-methylnaphthalene compound. The process is conducted under liquid phase conditions using a new complexing agent which is regiospecific for the beta position of naphthalene and which is an electron-rich, carbon-based compound. A preferred such agent is hexamethylbenzene. Also provided is a novel method for producing a 2-acetyl-6-methylnaphthalene compound of relative high purity from isomer mixtures by recrystallization from a hydrocarbon solvent, such as n-octane, isooctane, or n-nonane.

50 Claims, 1 Drawing Sheet

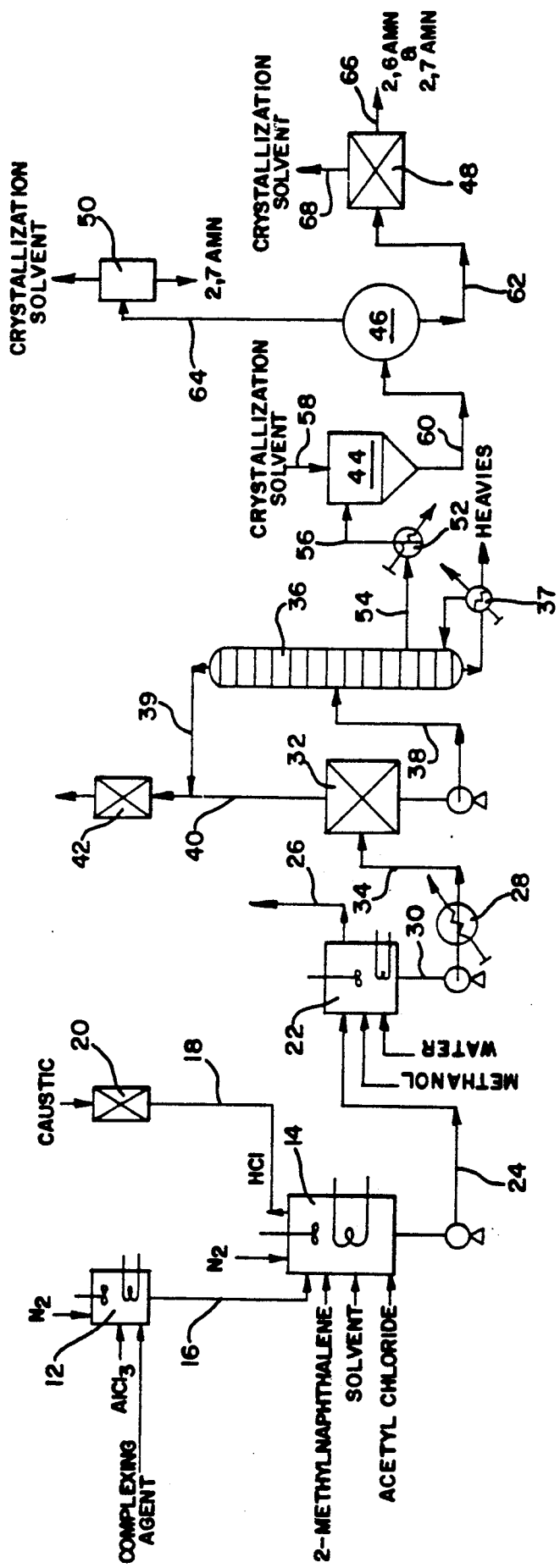

PREPARATION OF 2-ACYL-6-METHYLNAPHTHALENES

FIELD OF THE INVENTION

This invention relates to regioselective acylation of 2-methylnaphthalenes to 2-acyl-6-methylnaphthalenes.

BACKGROUND OF THE INVENTION

2-Acetyl-6-methylnaphthalene (2,6-AMN) and 2-acetyl-6,7-dimethylnaphthalene (2,6,7-ADMN) are useful feedstocks for the production of 2,6-naphthalene dicarboxylic acid and 2,3,6-naphthalene tricarboxylic acid, respectively, by oxidation. Such acids are useful monomers for polymerization into high performance resins (or so-called engineering resins).

2,6-AMN and 2,6,7-ADMN can be prepared by various synthetic routes. One promising route involves Friedel-Crafts acylation of the corresponding 2-methylnaphthalene (2-MN) and 2,3-dimethylnaphthalene (2,3-DMN).

Preparation of acyl aromatic ketones using Lewis-acid metallohalide catalysts has been research subject matter since the original discoveries of Friedel and Crafts reported in 1877. The use of a single solvent and complexing agent such as nitrobenzene to promote beta position substitution in Friedel-Crafts acylations of naphthalene ring systems has been known for many years. A synthesis of 2,6-AMN by condensing acetyl chloride with 2-MN in nitrobenzene is believed to have been first reported by Kon and Weller, J.Chem.Soc., 1939 792. The reaction is illustrated by the following equation:

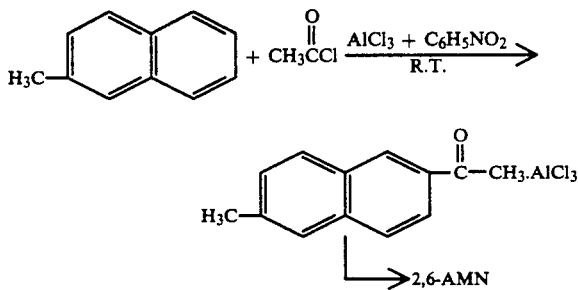

However, the reported isolated yield of 2,6-AMN was only 33 percent of theoretical. Since a 70 weight percent yield of the mixed isomeric ketones was isolated from the crude reaction mixture (by vacuum distillation), regiospecificity to the 2,6 isomer was characteristically undesirably low, probably on the order of about 50 percent.

A further disadvantage of this synthesis is that it requires the use of relatively large amounts of nitrobenzene which is undesirable particularly from a commercial processing standpoint because of the great toxicity of nitrobenzene. This material is categorized as a hazardous waste substance by the EPA. Thus, process waste water would have to be almost completely free of residual nitrobenzene to comply with EPA regulations.

An acylation procedure for 2-MN and for 2,3-DMN which would have high regiospecificity for producing beta position acylation and particularly the acetylation of the naphthalene nucleus, and which avoids the use of large amounts of nitrobenzene, would have value as a commercially practical procedure for making 2,6-AMN and 2,6,7-ADMN. The present invention provides such a procedure.

SUMMARY OF THE INVENTION

A regioselective process for making 2-acyl-6-methylnaphthalenes such as 2-acetyl-6-methyl naphthalene is provided wherein a 2-methylnaphthalene compound, such as 2-methylnaphthalene or 2,3-dimethylnaphthalene, is contacted in an acylation inert hydrocarbon solvent with an electron-rich complex constituted by a Friedel-Crafts catalyst, such as aluminum trichloride, a $C_2$—$C_5$ hydrocarbyl acylating agent such as acetyl chloride, and at least one carbon-based complexing agent which is regiospecific for the beta position of naphthalene and which has at least one electron-rich carbon center.

From the resulting reaction product mixture wherein, for example, acetyl chloride was used as the acylating agent, the Friedel-Crafts catalyst, the solvent, and the unreacted methylnaphthalene starting material are removed to produce an acetylmethylnaphthalene isomer mixture rich in a 2-acetyl-6-methylnaphthalene compound is separatable from such isomer mixture by fractional distillation and/or crystallization.

The carbon-based complexing agent can be a peralkylated aromatic hydrocarbon containing 12 to 22 carbon atoms, inclusive, a sterically hindered aliphatic hydrocarbon containing 4 to 22 carbon atoms, inclusive, a peralkylated metallocene, a peralkylated heterocyclic ring compound containing 5 to 18 ring atoms inclusive, and mixtures thereof. Presently preferred such complexing agents are the permethylated aromatic hydrocarbons, more preferably hexamethylbenzene.

The solvent is an acylation inert hydrocarbon that is liquid at 0° C., is a solvent for organic reactants and organic reaction products, and is a member of the group consisting of aromatic hydrocarbons, halohydrocarbons, and mixtures thereof. Preferably, the solvent also dissolves the catalyst; however, this is not essential.

A principal feature of the present invention is the use of an electron-rich, carbon-based complexing agent which promotes regiospecific electrophilic substitution reactions on aromatic compounds, particularly the acetylation of the beta position of naphthalene. Such complexing agents heretofore have not been utilized for this purpose. Their use in combination with an acylation inert hydrocarbon solvent avoids the toxicity and hazardous waste problems associated with prior art usage of nitrobenzene as the combined sole solvent and complexing agent in acylation reactions involving naphthalene.

Moreover, relatively small amounts of the complexing agent provided by the invention, dissolved in the medium of the reaction solution, are surprisingly effective in producing regiospecificity for the beta position of naphthalene. Such complexing agents heretofore have not been utilized for this purpose. Their use in combination with an acylation inert hydrocarbon solvent avoids the toxicity and hazardous waste problems associated with prior art usage of nitrobenzene as the combined sole solvent and complexing agent in acylation reactions involving naphthalene.

Another feature of the present invention is the provision of preferred procedures for admixing the reaction components so as to maximize yields and selectivities for 2,6-AMN and 2,6,7-ADMN while utilizing a complexing agent of this invention.

Yet another feature of the present invention is the provision of a simple and convenient novel procedure for separating the Friedel-Crafts catalyst from the reaction products with a minimum of exotherm. The procedure involves the admixture with such product mixture of a monohydric aliphatic alcohol containing 1 to 12 carbon atoms, inclusive, per molecule. A presently preferred such alcohol is a monoalkanol containing less than 5 carbon atoms per molecule. The most preferred alcohol for this purpose is methanol. Upon admixture, such an alcohol is believed to form a water soluble catalyst complex which is extracted with water from the reaction product mixture without decomposition of the catalyst into a gel. Preferably at least two water extractions are used to extract the catalyst.

A still further feature of the present invention is the provision of a reliable novel procedure for recovering relatively high purity 2-acetyl-6-methylnaphthalene from a mixture of isomers of acetylmethylnaphthalene. The present recovery procedure involves the dissolution of an isomer mixture rich in a 2-acetyl-6-methylnaphthalene in an alkane solvent containing 5 to about 20 carbon atoms per molecule. n-Octane and n-nonane are the preferred solvents. Particularly preferred as the solvent is n-nonane. The starting isomer mixture used for the recovery procedure can be directly derived from the acetylation reaction (with intervening removal of Friedel-Crafts catalyst, such as $AlCl_3$, solvent, and residual 2-methylnaphthalene starting material), or can be a bottoms residue from a fractional distillation procedure during which relatively high purity 2-acetyl-6-methylnaphthalene has been already recovered from the acetylation reaction products. After such a dissolution, the resulting solution is chilled, and then a crystallized 2-acetyl-6-methylnaphthalene is separated therefrom. Such a crystallization procedure is also believed to be useful for recovering a purified 2,6,7-ADMN.

Various other and further features, embodiments, and the like which are associated with the present invention will become apparent and better understood to those skilled in the art from the present description considered in conjunction with the accompanying drawings wherein presently preferred embodiments of the invention are illustrated, however, it is to be understood that the drawings and the associated accompanying portions of this specification are provided for purposes of illustration and description only, and are not intended as limitations on the invention.

BRIEF DESCRIPTION OF THE DRAWINGS

In the drawings:

FIG. 1 is a generalized flow diagram of a process embodying the present invention.

DETAILED DESCRIPTION OF PREFERRED EMBODIMENTS

The acylation and, preferably, acetylation reaction of the present invention is carried out under liquid phase conditions in the presence of a Friedel-Crafts catalyst, such as aluminum trichloride, which is present in a finely divided, dispersed or dissolved form.

While acetyl chloride is the preferred acylating agent for acylating the 2-methyl substituted naphthalene compounds by the processes of this invention, other hydrocarbyl acylating agents, and preferably $C_2$–$C_5$ hydrocarbyl acylating agents, are suitable. Therefore, although most of the discussion presented in this application concerns the acetylation of the 2-methyl substituted naphthalenes using acetyl chloride as the preferred acylating agent, it is to be understood that other acylating agents, particularly the $C_2$–$C_5$ hydrocarbyl acylating agents, can be employed for acylating the 2-methyl substituted naphthalenes.

A $C_2$–$C_5$ hydrocarbyl acylating agent, as the term is herein used, means that the acylating agent delivers an acyl group having two to five carbon atoms to the 2-methyl substituted naphthalene compounds even though the agent itself may contain more carbon atoms. Illustrative $C_2$–$C_5$ hydrocarbyl acylating agents are the acyl halides having two to five carbon atoms and being either straight-chain, branched, saturated or unsaturated in structure. Preferably, the halide is chlorine or bromine. For example, acetyl bromide, propionyl bromide, propionyl chloride, and the like. Other $C_2$–$C_5$ hydrocarbyl acylating agents include the anhydrides of carboxylic acids wherein the acid portion of the anhydride has two to five carbon atoms and wherein said acid portion is either branched, straight-chain, saturated or unsaturated, as, for example, acetic anhydride, propionic anhydride and the like. Mixed anhydrides are also suitable. Generally, when an anhydride is used as an acylating agent, a greater quantity of Friedel-Crafts catalyst is required as compared to when an acyl halide is used as an acylating agent.

As used herein, the term "Friedel-Crafts catalyst" includes not only aluminum chloride, but also other highly active metallic halides, including, for example, $AlBr_3$, $FeCl_3$, $FeBr_3$, $SbCl_5$, $SbBr_3$, $TiCl_4$, $NbCl_5$, $GaCl_3$, $ZrCl_4$, $BF_3$, $SbF_5$, $AsF_5$, and the like. The purity of the halide may exert a considerable influence on the yield of product; for example, trace amounts of ferric chloride with aluminum chloride can increase overall product yield, or exert an accelerating effect on the acylation reaction. Concentrated sulfuric acid and other mineral acids can be used with the acetyl chloride in a two phase system with ether. In general, any of the known Friedel-Crafts catalysts is believed to be useful in the regioselective process of this invention where a 2-methylnaphthalene compound is acetylated with acetyl chloride.

The carbon-based complexing agents of the present invention are thermally stable and are regiospecific for the beta position of naphthalene. Also, they have at least one electron-rich carbon center. They are characterized by:

(1) inability to undergo irreversible acylation with an acyl chloride in the presence of a Friedel-Crafts catalyst, and (2) ability to bind with the Friedel-Crafts catalyst.

Thus, such a complexing agent functions, when present, for example, during catalytic acylation of a 2-methylnaphthalene compound to a 2-acetyl-6-methylnaphthalene compound with acetyl chloride, to direct the production of a reaction product mixture containing an aromatic naphthalene ketone/Friedel-Crafts catalyst reaction product that is rich in 2-acetylnaphthalenes. Suitable such complexing agents can be drawn from among the various classes of electron-rich, carbon-based compounds above indicated. Such complexing agents are free from substituents, such as nitro groups, and the like.

As used herein, the term "2-methylnaphthalene compound" is generic to both 2-methylnaphthalene and 2,3-dimethylnaphthalene.

The term "thermally stable" as used herein in relation to a carbon-based complexing agent has reference to the fact that such a compound (or complexing agent) is stable and does not deteriorate, degrade, decompose, or the like at temperatures employed in the practice of the present invention, such as temperatures below about 70° C. (158° F.).

The term "peralkylated" as used herein in reference to a particular class of complexing agents, or to a specific complexing agent, denotes a complexing agent which is a carbon-based compound exhaustively alkylated with alkyl groups that contain 1 to 4 carbon atoms, inclusive. The term "exhaustively alkylated" does not mean that every carbon atom positioned on a molecule, such as an aromatic ring, is substituted by at least one such alkyl group, but rather that such a molecule is substituted with such alkyl groups to the extent possible before steric hindrance precludes further such substitution. Presently preferred peralkylated complexing agents of this invention are the permethylated aromatic hydrocarbon compounds.

Examples of suitable peralkylated aromatic hydrocarbons include those containing 12 to 22 carbon atoms inclusive per molecule, such as peralkylated benzenes like hexamethylbenzene, hexaethylbenzene, 1,3,5-tri(-tertbutyl)benzene, and the like, peralkylated naphthalenes like octamethylnaphthalene, and the like, and peralkylated diphenyl compounds like decamethyldiphenyl, and the like, can be used.

Examples of suitable sterically hindered aliphatic compounds include those containing 4 to 22 carbon atoms inclusive per molecule. Thus, cycloolefinic hydrocarbons containing no more than about 22 carbon atoms per molecule (and preferably containing at least two diene ring linkages per molecule) can be used, such as bicyclo [2.2.1] dienes, e.g., norbornadiene, hexamethylbicyclo [2.2.1] heptadiene, octamethylbicyclodienes, and the like; and peralkylated cyclodienes, e.g., pentamethylcyclopentadiene (preferred), and the like. Also, alkenes preferably containing about 4 to about 22 carbon atoms per molecule, such as 2,3-dimethyl-2-butene, 3-isopropyl-4-methyl-2-pentene, and the like, can be used.

Examples of suitable peralkylated metallocenes include bis(pentamethylcyclopentadienyl) ferrocene, bis(-pentamethylcyclopentadienyl) cobaltocene, bis(hexamethylcyclohexadienyl) ferrocene, bis(hexamethylcyclohexadienyl) cobaltocene, and the like.

Examples of suitable peralkylated heterocyclic ring compounds include those containing 5 to 18 ring atoms, inclusive, per molecule, such as peralkylated furans, peralkylated thiophenes, peralkylated pyrroles, peralkylated morpholines, peralkylated pyridines, and the like.

Examples of suitable peralkylated furans include tetramethyl furan, tetraethyl furan, and the like.

Examples of suitable peralkylated thiophenes include tetramethyl furan, tetraethyl furan, and the like.

Examples of suitable peralkylated pyrroles include tetramethyl pyrrole, tetraethyl pyrrole, and the like.

Examples of suitable peralkylated morpholines include tetramethylmorpholine, tetraethylmorpholine, and the like.

Examples of suitable peralkylated pyridines include pentamethylpyridine, pentaethylpyridine, and the like.

Because of the high basicity of the heteroatom in such peralkylated heterocylic compounds, such compounds are now believed to be less active than the other peralkylated compound classes indicated herein as complexing agents. Presently preferred complexing agents include hexamethylbenzene, octamethylnaphthalene, norbornadiene, pentamethylcyclopentadiene, 2,3-dimethyl butene, bis(pentamethylcyclopentadienyl)ferrocene, and pentamethylpyridine. Of these, hexamethylbenzene is presently a more preferred complexing agent.

The acetylation process of the present invention is carried out under liquid phase conditions. The reactants and the complexing agent(s) are contacted in an acylation inert hydrocarbon solvent that is a liquid at 0° C. (32° F.). The solvent solubilizes all reactants, the complexing agent(s), and optionally the catalyst. Also, the solvent exhibits chemical inertness towards the reactants and the characteristically strongly acidic catalyst system. The solvent also preferably dissolves the catalyst, but it is not necessary to impose this condition on a solvent because the acylation reaction will also proceed as a two-phase system wherein the catalyst, or a portion thereof, is in the form of an immiscible liquid, gel, or sludge in the liquid reaction solvent medium.

Presently preferred such solvents are selected from the group consisting of aromatic hydrocarbons, halohydrocarbons, and mixtures thereof.

Examples of suitable aromatic hydrocarbon solvents include benzene (presently preferred), lower alkyl substituted benzenes wherein each of the lower alkyl groups contains 1 to 4 carbon atoms, inclusive, and the like.

Examples of suitable halohydrocarbon solvents include methylene dichloride (presently preferred), 1,2-dichloroethane, and the like.

While mixtures of such solvents may be employed, if desired, solvent mixtures are not preferred since product separation on purification is simplified if only a single solvent is employed during an acetylation.

Each of the starting reactants 2-methylnaphthalene compound, and acetyl chloride) can be conventionally prepared or obtained commercially. It is presently preferred that each of such reactants, and also each of the other components including complexing agent and catalyst present in the reaction zone, have a purity of at least about 95 weight percent, and more preferably, a purity of at least about 99 weight percent.

The Friedel-Crafts catalyst such as aluminum chloride, the acetyl chloride, and the carbon-based complexing agent(s) are believed to form an electron-rich complex. To effect the desired acetylation, a catalytically effective amount of the Friedel-Crafts catalyst, e.g., aluminum trichloride, about 0.5 to about 5.0 equivalents of the complexing agent(s) per equivalent of the 2-methylnaphthalene compound, and about 0.5 to about 5 equivalents of the acetyl chloride per equivalent of such 2-methylnaphthalene compound are combined in an acylation inert solvent. In a preferred mode of practicing this invention, about 0.8 to about 1.2 equivalents of $AlCl_3$, per equivalent of the 2-methylnaphthalene compound, about 0.2 to about 2 equivalents of the complexing agent per equivalent of the 2-methylnaphthalene compound, and about 0.8 to about 1.2 equivalents of the acetyl chloride per equivalent of the 2-methylnaphthalene compound are combined in the solvent.

As a present preference, the weight ratio of solvent to 2-methylnaphthalene compound is in the range of about 1:1 to about 20:1; however, higher and lower such ratios can be employed without departing from the spirit and scope of this invention.

While the acylation reaction of the present invention wherein a 2-methylnaphthalene compound is combined with the electron-rich complex is preferably carried out at substantially room (ambient) temperature conditions, one skilled in the art will appreciate that temperatures somewhat elevated or lowered relative to room temperatures can be employed, if desired. For example, temperatures in the range of about 10° C. to about 40° C. (50° F. to 104° F.) are suitable, although higher and lower temperatures can be employed without departing from the spirit and scope of the present invention. However, at elevated temperature, yields of desired 2-acetyl-6-methylnaphthalenes may be reduced relative to the corresponding yields achieved at room temperatures, owing particularly to side reactions.

A process flow diagram illustrating the overall process for regioselective acetylation of 2-methylnaphthalenes to 2-acetyl-6-methylnaphthalenes is shown in FIG. 1. Mixing tank 12, equipped with cooling coils, is provided upstream from reactor 14 and serves as a vessel for the preparation of the electron-rich complex constituted by the catalyst and the carbon-based complexing agent. Mixing tank 12 communicates with reactor 14 by means of the complex feed line 16. Reactor 14 also communicates with catalyst quench tank 22 downstream via product line 24 and with caustic scrubber 20 via line 18.

Catalyst quench tank 22 receives an admixture of reaction product, reactants and catalyst complex through product line 24. An aqueous waste stream containing primarily a monohydric alcohol, such as methanol, the Friedel-Crafts catalyst, and water, is decanted from quench tank 22 through line 26 while an admixture of reaction products proceeds first to a heater means 28, such as a hot oil heater, via line 30 and then to flash distillation vessel 32 via line 34.

A bottom stream from flash distillation vessel 32, containing AMN isomers and some residual complexing agent, is fed via line 38 to vacuum distillation column 36 equipped with reboiler 37, while the flash distillation overhead product, chiefly constituted by the complexing agent and water and, optionally, the solvent, leaves the flash distillation vessel 32 via line 40 and passes through drier 42. Downstream from vacuum distillation column 36 are provided, in interconnected series, crystallizer 44, centrifuge 46 and drier 48.

A product cut, e.g., substantially the 2,6-AMN and the 2,7-AMN isomers, is withdrawn from column 36 through line 54 and passed to heat exchanger 52. Thereafter, the product cut is passed to crystallizer 44 via line 56. Solvent feed line 58 supplies a crystallization solvent to crystallizer 44. Product crystal-containing mother liquor from crystallizer 44 enters centrifuge 46 through line 60.

Crystalline product from centrifuge 46 is passed to drier 48 via line 62, and the recovered crystallization solvent is passed to liquid separator 50 via line 64. Dried product exits drier 48 via product line 66, and any crystallization solvent introduced into drier 48 along with the wet crystalline product via line 62 exits the drier 48 via line 68.

The present acetylation process can be practiced as a batch process as well as a continuous process. The exact manner in which the reactants, the catalyst, and the complexing agent(s) are brought together in solution in order to carry out the desired acetylation reaction appears to be relatively unimportant from the standpoint of achieving regiospecificity for the beta position of naphthalene using complexing agent(s) of this invention compared to results achieved under corresponding conditions without the use of a complexing agent of this invention. When a complexing agent of the present invention is present, the beta position selectivity achieved in this reaction is increased compared to the selectivity results obtained when the identical reaction is carried out in the absence of such complexing agent(s) but in a solvent as herein described.

In the practice of the present invention, it has been discovered that certain component admixing or addition procedures for bringing the components together at the time of acetylation reaction result in higher conversions and higher selectivities than other addition procedures.

For example, the following addition procedures were evaluated under similar reaction conditions:
  (a) addition of acetyl chloride to a solution of 2-MN, AlCl$_3$ and complexing agent (herein termed the Bouveault method);
  (b) addition of 2-MN to a solution of acetyl chloride, AlCl$_3$ and complexing agent (herein termed the Perrier method);
  (c) addition of AlCl$_3$ to a solution of 2-MN acetyl chloride and complexing agent (herein termed the Elbs method); and
  (d) addition of acetyl chloride to a solution of AlCl$_3$ followed by addition of the resulting solution to a solution of 2-MN and complexing agent wherein termed the retro-Perrier or solvated complex addition method).

In the retro-Perrier addition procedure, either the complexing agent can be dissolved with the Friedel-Crafts catalyst, such as aluminum trichloride, and the acetyl chloride, or the complexing agent can be dissolved with the 2-MN. In general, the location of the complexing agent need not be defined by the addition method; it is only required that the complexing agent be compounded with acetyl chloride, a Friedel-Crafts catalyst, such as aluminum trichloride, and the 2-methylnaphthalene compound. The retro-Perrier and the Elbs addition procedures appear to be about equally effective, and so such procedures are both preferred for purposes of practicing the present invention.

From the standpoint of achieving high conversion and high selectivity when acetylating 2-methylnaphthalene to produce 2-acetyl-6-methylnaphthalene, and as above indicated, one presently preferred addition procedure involves the above indicated retro-Perrier procedure in which a preformed solution of acetyl chloride and aluminum trichloride most preferably in methylene dichloride is added to a separately preformed solution of 2-MN and complexing agent in the same solvent. In such preferred addition procedure, methylene dichloride is the solvent for both such starting solutions, and the complexing agent is hexamethylbenzene.

Good results using such addition procedure were also obtained using hexamethylbenzene in methylene dichloride at a higher concentration of 2.4 equivalents hexamethylbenzene per equivalent 2-MN which was found to achieve a 70 percent selectivity to 2,6-AMN (other such equivalent ratios remaining the same), and a conversion to 2,6-AMN of about 95 percent (based on starting 2-MN) was achieved using this retro-Perrier addition method. Selectivity to 2,6-AMN from 2-MN using such addition procedure with ethylene dichloride solvent and hexamethylbenzene complexing agent is high, being typically in excess of about 60 percent, with corresponding conversions to 2,6-AMN from 2-MN also being high, such generally being in the range of about 80 to about 99 percent (based on starting 2-MN).

Another useful and preferred addition procedure is that herein termed the Elbs method which involves addition of aluminum trichloride in solution to a chilled solution of the reactants (2-MN and acetyl chloride) and the complexing agent(s) to initiate the acetylation. Good results, as shown by 66 percent selectivity and 72 weight percent conversion (based on starting 2-MN), were obtained with hexamethylbenzene as complexing agent and with methylene dichloride as solvent. Preferably the equivalent ratio of $AlCl_3$ to acetyl chloride to complexing agent is about 1:1:1.

Still another addition procedure is that herein termed the Perrier method wherein a solution of 2-MN is added to a solution of aluminum trichloride, acetyl chloride, and complexing agent (preferably hexamethylbenzene). The present preferred solvent is methylene dichloride. However, the Perrier addition procedure produces somewhat reduced yields and selectivity compared to the retro-Perrier method, possibly because of by-product formation.

The foregoing addition procedures also works for producing 2,6,7-ADMN from 2,3-DMN.

The presently more preferred complexing agent for use in the practice of this invention is hexamethylbenzene, a solid at ambient conditions. Yet, as the examples hereinbelow illustrate, when hexamethylbenzene was evaluated in various solvents as regards its capacity for beta directing during the acetylation of 2-MN with acetyl chloride and aluminum trichloride catalyst, excellent and unexpected high selectivity was achieved. For instance, in a benzene solution, relatively small amounts of hexamethylbenzene (2.4 equivalents/equivalent 2-MN) provided a substantial selectivity enhancement for 2,6-AMN from 2-MN as compared to benzene solvent alone. In particular, the presence of hexamethylbenzene provided a selectivity of about 52 percent, whereas in benzene alone, the selectivity was about 18 percent.

In a methylene dichloride solution, hexamethylbenzene (2.4 equivalents/equivalent 2-MN) provided a selectivity of about 66 percent. Selectivity in methylene dichloride alone was only about 9 percent.

In a 1,2-dichloroethane solvent, hexamethylbenzene (2.4 equivalents/equivalent 2-MN) exhibited a selectivity of about 63 percent:.

In all three such solvent systems (benzene, methylene dichloride, and 1,2-dichloroethare), selectivities to the two major by-products, 2,8-AMN (2-acetyl-8-methylnaphthalene) and 2,7-AMN (2-acetyl-7-methylnaphthalene), are significantly different for hexamethylbenzene as compared to, for example, nitrobenzene. The latter material exhibited low selectivity for such 2,7-isomer (8 to 11 percent) and relatively high selectivity for the 2,8-isomer (20 to 34 percent). Conversely, hexamethylbenzene exhibited higher selectivity for the 2,7-isomer (13 to 20 percent) and lower selectivity for the 2,8-isomer (9 to 17 percent). These differences indicate hexamethylbenzene operates differently from a material such as nitrobenzene as regards complexing capability and regioselective capability.

In acetylation procedures utilizing hexamethylbenzene as a complexing agent, reaction temperatures sufficient to keep the hexamethylbenzene in solution are needed. When the solvent is, for example, benzene, the reaction temperature utilized is in the range of ambient up to about 45° C. (113° F.) to keep the hexamethylbenzene in solution. At the end of an acetylation procedure, most of the hexamethylbenzene can be easily crystallized and then separated from dissolved reaction products either by chilling in the range of, for example, about 0° C. (32° F.) to about 10° C. (50° F.), or by partial evaporation of the solvent. In a commercial embodiment of the present invention, such a crystallization procedure provides a convenient and presently preferred technique for separation and reuse of such a complexing agent, as desired.

After the acetylation reaction, product separation and recovery procedures are implemented.

It is presently preferred to remove first from a liquid reaction product mixture that is believed to contain an aromatic ketone/Friedel-Crafts catalyst reaction product, preferably a mixture which contains substantially all of the Friedel-Crafts catalyst, such as aluminum trichloride. If and when the catalyst is not fully dissolved, and so is present in the liquid reaction product medium at least in part as particulate matter, then the liquid reaction product can be separated from such particulate matter by a conventional solids/liquid separation procedure, such as filtration, centrifuging, or the like.

A presently more preferred procedure for separating the dissolved catalyst is to add to a liquid reaction product a water-extractable aliphatic monohydric alcohol containing up to about 12 carbon atoms per molecule, inclusive, as a solubilizing agent. Preferred such alcohols are the monoalkanols containing 1 to 4 carbon atoms per molecule.

Examples of such alcohols include methanol, ethanol, propanol, isopropanol, the butanols, and the like. Particularly preferred for this purpose is methanol.

The alcohol forms a water-soluble complex with the catalyst which complex is subsequently readily extractable from the resulting liquid and mixture without decomposition of the Friedel-Crafts catalyst, i.e., $AlCl_3$, into a gel, or the like.

A presently preferred procedure involves adding, with agitation, about 1 to about 5 equivalents of the alcohol per equivalent of catalyst to such a liquid product reaction mixture. A two-phase admixture is produced in which the relatively lighter aqueous phase comprises extracted alcohol/catalyst complex in an aqueous solution, and the relatively heavier phase is an organic liquid phase containing the product. Preferably, the quantity of water so added is at least sufficient to produce an aqueous phase which, after phase separation, is at least equal in volume to the volume of the organic liquid phase.

The aqueous phase is isolated and can be discarded. The remaining organic liquid phase can be extracted one or more additional times in a similar manner. The ultimately isolated organic liquid phase comprises a solution of solvent, complexing agent, unreacted 2-methylnaphthalene compound, and the product 2-acetyl-6-methylnaphthalene isomer mixture.

Those skilled in the art will appreciate that, as an alternative to the above described preferred procedure of alcohol/catalyst complex formation followed by water extraction, one of the various Friedel-Crafts catalyst separation procedures known to the prior art may be used if desired in order to isolate the product-containing organic liquid phase. For example, either concentrated hydrochloric acid or concentrated ammonium hydroxide may be added to a liquid product mixture for achieving complex formation thereof with the aluminum trichloride. If the resulting exotherm is undesirable, it can be reduced by slow addition of the reactants or by cooling.

For example, concentrated hydrochloric acid can be admixed with a reaction product mixture with crushed ice.

For another example, a concentrated ammonium hydroxide can be admixed with a chilled reaction product mixture.

Thereafter, the resulting system, whether containing concentrated HCl or concentrated NH$_4$OH, is extracted with an organic solvent, such as methylethyl ether, diethyl ether, or the like.

After mixing or otherwise accomplishing formation of an aqueous liquid containing an extractable alcohol/catalyst complex, the catalyst containing layer is conventionally separated from the organic layer containing the desired product. The resulting desired organic layer can then be further washed with water, if desired. The resulting washed organic layer can be dried by conventional means, e.g., with magnesium sulfate, or the like, filtered, and subjected to evaporation so as to remove at least about one-half of the organic solvent liquid present. Evaporation can be carried out using a conventional rotary evaporator, or the like.

After removal of the catalyst, the complexing agent(s), solvent, and residual 2-MN are separated and removed from the 2-acetyl-6-methylnaphthalene product isomer mixture. No special procedure need be used for separation of solvent, residual complexing agent, and residual 2-MN.

The obtained mixture of the various acetylmethylnaphthalene isomers is subjected to separation procedure(s) to recover therefrom a desired high purity 2-acetyl-6-methylnaphthalene product. Any convenient isomer mixture separation technique can be employed, including a combination of flash distillation, fractional distillation, and crystallization; or the like.

When 2-methylnaphthalene is the starting material, the product isomer mixture is rich in 2-acetyl-6-methylnaphthalene. The principal additional isomers present are 2-acetyl-8-methylnaphthalene, 2-acetyl-1-methylnaphthalene, and 2-acetyl-7-methylnaphthalene.

When 2,3-dimethylnaphthalene is the starting material, the product isomer mixture is rich in 2-acetyl-6,7-dimethylnaphthalene. The principal other isomers present are not presently known.

In the case of each such isomer mixture, fractional distillation is a convenient procedure that can be employed to produce a product of a desired purity level. For reasons of subsequent processing, e.g., oxidation to the corresponding carboxylic acid, and of ultimate product utilization, a product purity of at least about 95 weight percent is presently preferred for each of the isolated 2,6-AMN and 2,6,7-ADMN.

A 95 weight percent pure 2,6-AMN product is characteristically comprised of at least about 95 weight percent 2,6-AMN with the remainder thereof being primarily the 2,7-AMN isomer, while a 95 weight percent pure 2,6,7-ADMN product is characteristically comprised of at least about 95 weight percent 2,6,7-ADMN with the remainder thereof being other presently unidentified isomers.

In one aspect, the present invention provides a new and very useful method for obtaining 2,6-AMN of relatively high purity and in relatively high yield. This method involves recrystallization using as a solvent an alkane containing 5 through 20 carbon atoms per molecule. Presently preferred such alkanes for use in producing a 2,6-AMN product are n-octane, isooctane, and n-nonane (presently most preferred). A similar method is also presently believed to be useful for obtaining 2,6,7-ADMN in relatively high purity and in relatively high yield.

Any convenient acetylmethylnaphthalene isomer mixture may be used as a starting composition for the present recrystallization process. A present preference is to employ either the starting isomer mixture produced from the hereinabove described acetylation followed conveniently by a separation procedure, such as hereinabove indicated, or an isomer mixture derived from another source, e.g., from a fractional distillation, or the like.

In one presently preferred mode of recovery of 2,6-AMN, a vacuum fractional distillation of a starting isomer mixture is carried out to remove almost all of the 2,8-AMN and preferably also some of the 2,7-AMN. Preferably the recovered isomer mixture contains at least about 87 weight percent of 2,6-AMN. Since the 2,7-AMN has a boiling point that is very close to that of the 2,6-AMN, it is not always economical or practically possible to upgrade all of the product 2,6-AMN to 95 percent purity level by distillation alone. In view of this circumstance, a side stream from the reboiler of the fractional distillation column can be continuously separated during the distillation recovery procedure. Such a stream typically contains about 87 weight percent 2,6-AMN and about 13 weight percent 2,7-AMN on a 100 weight percent total stream basis. This stream can then be collected and purified by the recrystallization process as presently taught herein.

In another procedure, such as when a fractional distillation is either not practical, or not economically feasible, the entire initially produced isomer mixture can be purified by the aforedescribed recrystallization process to achieve the desired 95 weight percent pure 2,6-AMN recovered product.

This recrystallization procedure involves preliminary dissolution of the isomer mixture in an alkane, such as n-nonane (preferably most preferred). Preferably, the isomer mixture is one which has been produced by a preliminary fractional distillation of a starting isomer mixture, as above described, and the residue is used for the present fractional distillation of a starting isomer mixture. A present preference is to employ a weight ratio of isomer mixture to alkane solvent in the range of about 0.1 to about 2, although larger and smaller such ratios may be used, if desired. At the time of dissolution, the temperature of the isomer mixture and of the alkane is preferably in the range of about 25° to about 90° C. (80° to 200° F.), although higher and lower such temperatures may be employed, if desired.

After such dissolution, the product solution is chilled, preferably to a temperature in the range of about 0° C. to about 25° C., (35° F. to 80° F.), although higher and lower temperatures can be employed, if desired. The chilling results in the formation of crystals of purified 2,6-AMN which can be separated as desired, usually by filtration or centrifuging.

For example, for an isomer mixture feed containing 87.6 weight percent 2,6-AMN with the remainder being mainly 2,7-AMN, a product of the desired minimal approximately 95 weight percent purity in a yield over 95 weight percent (based on 2,6-AMN) can be obtained by a crystallization technique in n-nonane at about 60° F. (15.6° C.) at a 2:1 solvent-to-isomer mixture weight ratio. Solids/liquid separation of crystallized solids can be accomplished by filtration, centrifuging, or the like, as desired.

For another example, an isomer mixture freshly obtained directly from acetylation followed by a separation procedure, such as above indicated, and which contains a relatively lower concentration of 2,6-AMN can be purified to the desired 95 weight percent purity 2,6-AMN in a multi-step crystallization procedure. Thus, such a starting isomer mixture is dissolved, preferably in n-nonane, at 38° C. (100° F.) followed by cooling, crystal formation, and separation. The separated product is then redissolved with same solvent at about the same temperature, preferably in n-nonane at about 38° C. (100° F.), followed again by cooling, crystal formation and separation. Using a two-step procedure, an overall yield of about 85 weight percent is obtainable (based on starting 2,6-AMN present in the starting isomer mixture) of at least about 95 weight percent purity 2,6-AMN.

A comparison of the alkanes n-octane, n-nonane, and n-decane as solvents for recrystallization of 2,6-AMN in accord with the present invention is provided below. In general, experience indicates that n-nonane is better at separating 2,7-AMN without losing 2,6-AMN than any other known solvent; hence, the present preference for n-nonane as the solvent for recrystallization.

Isooctane is also a fairly effective medium for purifying 2,6-AMN as exemplified below. However, purities in excess of about 95 weight percent for 2,6-AMN appear to be difficult to obtain using isooctane as solvent because its relative selectivity towards 2,7-AMN in comparison to, or in relation to, 2,6-AMN is not as good as that of n-octane or n-nonane.

An evaluation of various possible alternative solvents as possible media for recrystallization of 2,6-AMN was carried out as exemplified below.

The following examples are offered to specifically illustrate this invention. These examples are not to be construed as limiting the scope thereof, however.

In each of the following examples, unless otherwise indicated, the reaction flask wherein the condensing of acetyl chloride with 2-methylnaphthalene compound occurred was initially cooled in an ice bath (0° C.) to compensate for the exothermicity of reaction. After combination of all reactants, the flask was allowed to warm to room temperature for the remainder of the reaction.

EXAMPLE 1

Synthesis of 2-acetyl-6-methylnaphthalene by acetylation of 2-methylnaphthalene without complexing agent To a stirred round bottom flask was added 1.70 g (12.7 mmol) of AlCl$_3$ and then 5 ml of benzene. To this mixture was added 25 ml of benzene as solvent which resulted in the formation of a clear solution. The flask and its contents were chilled in an ice bath. Then, 1.81 g (12.7 mmol) of 2-methylnaphthalene was added all at once, and, after such was completely dissolved, 1.00 g. (12.7 mmol) of acetyl chloride was added dropwise over a period of several minutes which resulted in the formation of a dark solution. The resulting solution was allowed to warm to room temperature. After one hour of stirring, 1 ml of this slurry was quenched in 2 ml of concentrated ammonium hydroxide, shaken, and extracted with about 4 ml of diethyl ether. The subsequently separated ether solution was evaporated to about ½ of its original volume and analyzed in a gas liquid chromatograph. After 19 hours of further continuous stirring, another 1 ml of the reaction mixture was quenched and analyzed. The conversion and selectivity achieved are shown in Table I below, such values being estimated based on a well known G.C. area percent analytical method.

In this procedure, and, in general, for all the exemplary procedures reported herein, both conversion and selectivity were substantially unchanged between their respective values after one hour of the acetylation and after 17-24 hours of such acetylation.

EXAMPLE 2

Synthesis of 2-acetyl-6-methylnaphthalene by acetylation of 2-methylnaphthalene with hexamethylbenzene as complexing agent To a stirred round bottom flask was added 1.81 g (12.7 mmol) of 2-methylnaphthalene, 5.0 g of hexamethylbenzene (30.8 mmol), 25 ml benzene, and 1.00 g (12.7 mmol) of acetyl chloride which resulted in a clear colorless solution. The flask and its contents were chilled in an ice bath. To this flask was added 1.70 g (12.7 mmol) of aluminum chloride in small increments over a period of 5 minutes which resulted in a dark colored reaction mixture. The resulting solution was allowed to warm to room temperature. This solution was sampled, quenched and analyzed by the same procedure employed in Example 1 at 1 hour and also at 17 hours of reaction time. The conversion and selectivity achieved are shown in Table I below, and such values were estimated by the G.C. area percent analytical method indicated in Example 1.

EXAMPLE 3

Synthesis of 2-acetyl-6-methylnaphthalene by acetylation of 2-methylnaphthalene without complexinq agent To a stirred round bottom flask was added 1.70 g (12.7 mmol) of AlCl$_3$ and then 5 ml of methylene dichloride. To this mixture was added 25 ml of methylene dichloride as solvent which resulted in the formation of a clear solution. The flask and its contents were chilled in an ice bath. Then 1.81 g (12.7 mmol) of 2-methylnaphthalene was added all at once, and, after it was completely dissolved, 1.00 g (12.7 mmol) of acetyl chloride was added dropwise over a period of several minutes which resulted in the formation of a dark solution. The resulting solution was allowed to warm to room temperature. After one hour of stirring, 1 ml of this slurry was quenched in 2 ml of concentrated ammonium hydroxide, shaken, and extracted with about 4 ml of methylethyl ether. The subsequently separated ether solution was evaporated to about ½ of its original volume and analyzed by gas liquid chromatograph. After 19 hours of further continuous stirring, another 1 ml of the reaction mixture was quenched and analyzed. The conversion and selectivity achieved are shown in Table I below. Such values were estimated based on the G.C. area percent analytical method of Example 1.

EXAMPLE 4

Synthesis of 2-acetyl-6-methylnaphthalene by acetylation of 2-methylnaphthalene with hexamethylbenzene as complexing agent To a stirred round bottom flask was added 1.81 g (12.7 mmol) of 2-methylnaphthalene, 5.0 g of hexamethylbenzene (30.8 mmol), 25 ml methylene dichloride, and 1.00 (12.7 mmol) of acetyl chloride which resulted in a clear colorless solution. The flask and its contents were chilled in an ice bath. To this was added 1.70 g (12.7 mmol) of aluminum chloride in small increments over a period of 5 minutes which resulted in a dark reaction mixture. The resulting solution was allowed to warm to room temperature. This solution was sampled, quenched and analyzed by the same procedure employed in Example 1 at 1 hour and at 17 hours of reaction time. The conversion and selectivity achieved are shown in Table I below, and such values were estimated by the G.C. area percent analytical method indicated in Example 1.

EXAMPLE 5

Synthesis of 2-acetyl-6-methylnaphthalene by acetylation of 2-methylnaphthalene without complexing agent To a stirred round bottom flask was added 1.70 g (12.7 mmol) of AlCl$_3$ and then 5 ml of ethylene dichloride. To this mixture was added 25 ml of ethylene dichloride as solvent which resulted in the formation of a clear solution. The flask and its contents were chilled in an ice bath. Then 1.81 g (12.7 mmol) of 2-methylnaphthalene was added all at once, and, after it was completely dissolved, 1.00 g (12.7 mmol) of acetyl chloride was added dropwise over a period of several minutes which resulted in the formation of a dark solution. The resulting solution was allowed to warm to room temperature. After one hour of stirring, 1 ml of this slurry was quenched in 2 ml of concentrated ammonium hydroxide, shaken, and extracted with about 4 ml of methyl ethyl ether. The subsequently separated ether solution was evaporated to about ½ of its original volume and analyzed by gas liquid chromatograph. After 19 hours of further continuous stirring, another 1 ml of the reaction mixture was quenched and analyzed. The conversion and selectivity achieved are shown in Table I below, and such values were estimated based on the G.C. area percent analytical method of Example 1.

EXAMPLE 6

Synthesis of 2-acetyl-6-methylnaphthalene by acetylation of 2-methylnaphthalene with hexamethylbenzene as complexing agent To a stirred round bottom flask was added 1.81 g (12.7 mmol) of 2-methylnaphthalene, 5.0 g of hexamethylbenzene (30.8 mmol), 25 ml ethylene dichloride, and 1.00 g (12.7 mmol) of acetyl chloride which resulted in a clear colorless solution. The flask and its contents were chilled in an ice bath. To this was added 1.70 g (12.7 mmol) of aluminum chloride in small increments over a period of 5 minutes which resulted in a dark reaction mixture. The resulting solution was allowed to warm to room temperature. This solution was sampled, quenched and analyzed by the same procedure employed in Example 1 at 1 hour and at 17 hours of reaction time. The conversion and selectivity achieved are shown in Table I below, and such values were estimated by the G.C. area percent analytical method indicated in Example 1.

TABLE I

| | | Comparative Evaluation of Complexing Agents | | | | |
|---|---|---|---|---|---|---|
| Ex. No. | Solvent System | Addition Method | % Conversion 2-MN | % Select. to AMN | | |
| | | | | 2,6 | 2,8 | 2,1 |
| 1 | benzene (30 ml) | B | 85 | 18 | 45 | 27 |
| 2 | benzene (25 ml) + HMB (2.4 eq) | E | 85 | 52 | 17 | 20 |
| 3 | CH$_2$Cl$_2$ (25 ml) | B | 84 | 9 | 26 | 62 |
| 4 | CH$_2$Cl$_2$ (25 ml) + HMB (2.4 eq) | E | 72 | 66 | 9 | 13 |
| 5 | (CH$_2$)$_2$Cl$_2$ (25 ml) | B | 86 | 21 | 27 | 42 |
| 6 | (CH$_2$)$_2$Cl$_2$ (25 ml) + HMB (2.4 eq) | E | 92 | 63 | 10 | 16 |

General Notes for Table I (all examples):
Reaction temperature: 0° C. (32° F.) initial, 20° C. (68° F.) terminal
Reaction Time: 1 hr.
Addition Method B: acetyl chloride added to other reactants (Bouveault addition method)
Addition Method E: AlCl$_3$ added to other reactants (Elbs addition method)
Reaction stoichiometries (all): 1/1/1 for 2-MN/acetyl chloride/AlCl$_3$

EXAMPLE 7

Acetylation of 2-methylnaphthalene with AlCl$_3$ and Hexamethylbenzene Complexing Agent using Retro-Perrier Addition Procedure 1.70 g (12.7 mmol) Aluminum chloride and 1.00 g (12.7 mmol) of acetyl chloride were successively dissolved in 10 ml methylene dichloride. The resulting solution was added to a solution of 20 ml methylene dichloride containing 1.81 g (12.7 mmol) of 2-methylnaphthalene and 2.0 g (12.3 mmol) hexamethylbenzene.

The resulting solution was allowed to warm to room temperature. This reaction mixture was sampled, quenched, and analyzed at 1 hour and at 24 hours elapsed time.

The results are summarized in Table II below.

EXAMPLE 8

Acetylation of 2-methylnaphthalene with methylene dichloride

The procedure of Example 7 was repeated except that the hexamethylbenzene was omitted and a larger amount of methylene dichloride was used. The solvent volume to weight ratio of 2-MN in methylene dichloride was about 16.6.

The results are summarized in Table II below.

TABLE II

Behavior of Hexamethylbenzene as Complexing Agent in Methylene Dichloride as Affecting Isomer Selectivity of AMN's

| Ex. No. | Medium | % 2-MN Conv. | % Selectivity to 2,1- | 2,8- | 2,7- | 2,6- | Sum | Other |
|---|---|---|---|---|---|---|---|---|
| 7 | 1 eq. HMB* in CH$_2$Cl$_2$ | 90.6 | 8.93 | 13.26 | 6.81 | 65.74 | 94.74 | 5.26 |
| 8 | CH$_2$Cl$_2$ | 83.8 | 61.86 | 25.65 | | 8.68 | 96.19 | 3.81 |

Table II General Notes:
*HMB = Hexamethylbenzene
Reaction Temperature = 0° C. (32° F.) initial, 20° C. (68° F.) final
Reaction Time = 1 hour
Addition = acetyl chloride + AlCl$_3$ added to other reactants (retro-Perrier addition method)
Solvent Ratio = 16.6 ml methylene dichloride gm 2-MN

EXAMPLES 9.1–9.11

Recrystallization of 2,6-AMN from n-nonane Solution of Isomer Mixture

Each one of the series of starting mixed isomer mixtures individually containing an amount of 2,6-AMN as shown in Table III, below, with the balance thereof being substantially 2,7-AMN, was individually dissolved in n-nonane at a respective temperature and a weight ratio of n-nonane to isomer mixture as shown in Table III. Thereafter, each solution was cooled to about 60°–70° F. (15.5–21.0° C.) and the crystallized product solids produced were separated therefrom. In some cases, such product was washed in n-nonane. The weight percent of 2,6-AMN in each recovered product was determined. The weight percent of the 2,6-AMN in the starting isomer mixture, or yield, is shown in Table III, below, together with the processing conditions.

TABLE III 2,6-AMN Recrystallization from n-Nonane

| Ex. No. | 2,6-AMN Content of Starting Mixture Wt. % (1) | Solvent to Mixture Weight Ratio and Temp. | Wash | Wt. % of 2,6-AMN in Product | Yield of 2,6-AMN Recovered % |
|---|---|---|---|---|---|
| 9.1 | 73.7 | 1:1 70° F. | X | 77.9 | 96.7 |
| 9.2 | 73.7 | 2:1 70° F. | X | 85.2 | 72.7 |
| 9.3 | 73.7 | 3:1 70° F. | X | 92.6 | 69.6 |
| 9.4 | 73.7 | 4:1 60° F. | X | 94.1 | 70.8 |
| 9.5 | 73.7 | 4:1 60° F. | 3:1 40° F. | 98.9 | 71.3 |
| 9.6 | 87.6 | 4:1 70° F. | 3:1 40° F. | 99.4 | 73.3 |
| 9.7 | 87.6 | 4:1 60° F. | 3:1 40° F. | 99.2 | 74.5 |
| 9.8 | 87.6 | 3:1 60° F. | 3:1 40° F. | 98.7 | 80.9 |
| 9.9 | 87.6 | 2:1 70° F. | 3:1 40° F. | 94.5 | 90.7 |
| 9.10 | 73.7 | 2:1 60° F. | X | 85.2 | 87.5 |
| 9.11 | 87.6 | 2:1 60° F. | X | 94.4 | 96.8 |

Table III Footnote:
(1) Balance of starting isomer mixtures is comprised of 2,7-AMN.

EXAMPLE 10

Recrystallization of 2,6-AMN from n-Nonane Solution of Isomer Mixture

A crude isomer mixture weighing 33.71 grams and containing 59.4 weight percent 2,6-AMN, 12.8 weight percent nitrobenzene and 27.8 weight percent of other materials which were believed to be mainly other isomers of acetylmethylnaphthalene was used for the present evaluation.

This isomer mixture is dissolved in 150 ml (105.45 g) of n-octane at 70° F. (21.1° C.) and cooled to about 45° F. (7° C.) where crystals were formed and separated.

After two washes of the recovered crystals with n-octane at 45° F. (7.22° C.) the first wash using ml of n-octane, and the second wash using 10 ml of n-octane, 14.34 grams of recrystallized solids were recovered.

The mother liquor was subjected to evaporation using a rotary evaporator and was thus concentrated to a residual weight of 19.37 grams.

The results are summarized in Table IV below:

TABLE IV

Recrystallization of 2,6-AMN in n-Octane

| Wt. % 2,6-AMN in starting mixture | Ratio of Solvent to starting isomer mixture | Wash Weight ratio of solvent to crystallized product | Wt. % of 2,6-AMN in Product | Yield of 2,6-AMN, % |
|---|---|---|---|---|
| 59.4% (12.8% NB) | 4.5:1 @ 70° F. | (1) 0.14:1 (2) 0.49:1 both @ 45° F. | 86.6% | 62.1% |

EXAMPLE 11

Comparison of n-Octane, n-Nonane, and n-Decane as Solvents

An isomer mixture of the following analysis was used:

| Isomer Mixture Component | Wt. % (Total Wt. Basis) |
|---|---|
| 2,6-AMN | 87.60 |
| 2,7-AMN | 9.60 |
| Other Isomers | 2.80 |
| (Total) | 100.00 |

4-gram samples of this isomer composition were dissolved in each of n-octane, n-nonane and n-decane at a 3:1 weight ration of solvent to isomer mixture at 100° F. (38° C.). The solution was then cooled to about 60° F. (15.5° C.) where a crystallized product formed and was separated. In each case, this product was washed with 12 grams of the same solvent at 40° F. (4.44° C.). The yields of respective isomers recovered in the respective products after analysis thereof was found to be as follows:

TABLE V

Comparison of n-Octane, n-Nonane and n-Decane as Solvents

| Solvent | AMN Isomer in Recovered Product, Wt. % | | | Yield of 2,6-AMN Recovered, % |
|---|---|---|---|---|
| | 2,6 | 2,7 | 2,8 | |
| n-octane | 97.5 | 2.1 | .2 | 78.3 |
| n-nonane | 98.2 | 1.8 | 0 | 85.6 |
| n-decane | 96.4 | 3.6 | 0 | 72.4 |

While all these solvents were suitable, based upon the foregoing results, n-nonane gave the highest yield.

EXAMPLE 12

Comparison of n-Octane and n-Nonane

A mixed AMN isomer mixture having the following composition was used:

| Isomer Mixture Component | Wt. % (total Wt. Basis) |
|---|---|
| 2,6-AMN | 73.7% |
| Other Isomers | 26.3% |

Four gram samples of the isomer mixtures were dissolved in each of n-octane and n-nonane at a 4:1 weight ratio of solvent to isomer mixture at 100° F. (38° C.) where a crystallized product formed and was separated. The product was not washed. The yields of respective isomers recovered in the respective products after analysis thereof was found to be as follows:

TABLE VI

Comparison of n-Octane and n-Nonane as Solvent

| Solvent | AMN Isomer in Recovered Product, Wt. % | | | Yield of 2,6-AMN Recovered, % |
|---|---|---|---|---|
| | 2,6 | 2,7 | 2,8 | |
| n-octane | 92.7 | 3.2 | 2.2 | 63.7 |
| n-nonane | 94.1 | 2.7 | 1.7 | 70.8 |

As the data shown in Tables V and VI demonstrates, n-nonane was found to be the better recrystallization solvent under the conditions employed.

EXAMPLE 13

Recrystallization with Isooctane

A series of acetylmethylnaphthalene isomer mixtures, each one containing a different amount of 2,6-AMN, were recrystallized with isooctane.

Each sample was dissolved in isooctane at the temperature shown in Table VII below and then cooled to the temperature shown in Table VII below. Crystallized solids were separated therefrom. Thereafter, each so produced solid particulate product was washed with an additional quantity of the same solvent. The washed product was analyzed. Results are shown in Table VII, below:

TABLE VII

Solubility of Mixed Isomers in Isooctane

| Starting 2,6-AMN (1) | Dissolution | | | Wash | | |
|---|---|---|---|---|---|---|
| | Solvent to Isomer Mixture Weight Ratio | Temp. of Dissol. | Solvent to Crystal Weight Ratio | Wash Temp. | Wt. % of 2,6-AMN in Crystallized Product | Yield of 2,6-AMN Recov'd, % |
| 73.7 | 3:1 | 70° F. | 1:1 | 70° F. | 90.0 | 65.9 |
| 73.7 | 2:1 | 70° F. | 1:1 | 70° F. | 86.9 | 81.9 |
| 73.7 | 3:1 | 70° F. | 1:1 | 70° F. | 87.4 | 76.6 |
| 73.7 | 4:1 | 60° F. | 1:1 | 70° F. | 85.6 | 79.3 |
| 73.7 | 3:1 | 50° F. | 1:1 | 70° F. | 84.0 | 81.7 |
| 83.0 | 4:1 | 70° F. | 1:1 | 70° F. | 93.4 | 88.0 |
| 83.0 | 3:1 | 70° F. | 1:1 | 70° F. | 92.8 | 89.6 |

Table VII Footnote:
(1) Indicates 2,6-AMN content in starting isomer mixture, wt. %.

The foregoing specification is intended as illustrative and is not to be taken as limiting. Still other variations within the spirit and the scope of the invention are possible and will readily present themselves to those skilled in the art.

We claim:

1. A process for making a 2-acetyl-6-methylnaphthalene compound which comprises the steps of:
(A) combining
   a 2-methylnaphthalene compound selected from the group consisting of 2-methylnaphthalene and 2,3-dimethylnaphthalene with
   an electron-rich complex constituted by a Friedel-Crafts catalyst, acetyl chloride, and at least one carbon-based complexing agent which has at least one electron-rich carbon center and is selected from the group consisting of a peralkylated aromatic hydrocarbon compound containing 12 to 22 carbon atoms, inclusive, per molecule; a sterically hindered aliphatic hydrocarbon compound containing 4 to 22 carbon atoms, inclusive, per molecule; a peralkylated metallocene compound; a peralkylated heterocyclic ring compound containing 5 to 18 ring atoms, inclusive, per molecule; in an inert organic solvent that is liquid at 0° C. so as to produce a reaction mixture containing an aromatic ketone/Friedel-Crafts catalyst reaction product;
(B) contacting said reaction mixture with a solubilizing agent to complex said Friedel-Crafts catalyst to produce a water-extractable catalyst complex wherein said solubilizing agent is a monohydric aliphatic alcohol containing 1 to 12 carbon atoms, inclusive; and
(C) removing said catalyst complex from said reaction mixture to produce a 2-acetyl-6-methylnaphthalene-rich acetylmethylnaphthalene isomer mixture.

2. The process of claim 1 wherein said 2-methylnaphthalene compound is 2-methylnaphthalene and said isomer mixture is rich in 2-acetyl-6-methylnaphthalene.

3. The process of claim 1 wherein said 2-methylnaphthalene compound is 2,3-dimethylnaphthalene and said isomer mixture is rich in 2-acetyl-6,7-dimethylnaphthalene.

4. The process of claim 1 wherein said electron-rich complex consists essentially of
 a catalytically effective amount of aluminum trichloride,
 about 0.5 to about 5 equivalents said complexing agent per equivalent of said 2-methylnaphthalene compound, and
 about 0.5 to about 5 equivalents of said acetyl chloride per equivalent of said 2-methylnaphthalene compound.

5. The process of claim 1 wherein said complexing agent comprises a said peralkylated aromatic hydrocarbon compound that is selected from the group consisting of peralkylated benzenes, peralkylated naphthalenes, and peralkylated biphenyl compounds.

6. The process of claim 5 wherein said peralkylated aromatic hydrocarbon compound is permethylated.

7. The process of claim 6 wherein said permethylated aromatic hydrocarbon compound is hexamethylbenzene.

8. The process of claim 6 wherein said permethylated aromatic hydrocarbon compound is octamethylnaphthalene.

9. The process of claim 1 wherein said complexing agent comprises a said sterically hindered aliphatic hydrocarbon compound that is selected from the group consisting of alkenes, bicyclo [2.2.1]dienes, and peralkylated cyclodienes.

10. The process of claim 9 wherein said sterically hindered aliphatic hydrocarbon compound is norbornadiene.

11. The process of claim 9 wherein said sterically hindered aliphatic hydrocarbon compound is pentamethylcyclopentadiene.

12. The process of claim 9 wherein said sterically hindered aliphatic hydrocarbon compound is 2,3-dimethyl-2-butene.

13. The process of claim 1 wherein said complexing agent comprises a said peralkylated metallocene compound selected from the group consisting of bis(pentamethylcyclopentadienyl) ferrocene, bis(pentamethylcyclopentadienyl) cobaltocene, bis(hexamethylcyclohexadienyl) ferrocene, and bis(hexamethylcyclohexadienyl) cobaltocene.

14. The process of claim 1 wherein said complexing agent comprises a said peralkylated heterocyclic ring compound selected from the group consisting of peralkylated furans, peralkylated thiophenes, peralkylated pyrroles, peralkylated morpholines, and peralkylated pyridines 15. The process of claim 14 wherein said peralkylated heterocyclic ring compound is permethylated.

16. A regioselective process for making a 2-acetyl-6-methylnaphthalene compound which comprises the successive steps of
 (A) combining
  a 2-methylnaphthalene compound selected from the group consisting of 2-methylnaphthalene and 2,3-dimethylnaphthalene with
  an electron-rich complex constituted by aluminum trichloride, acetyl chloride, and at least one carbon based complexing agent which has at least one electron-rich carbon center, and which is selected from the group consisting of a peralkylated aromatic hydrocarbon compound containing 12 to 22 carbon atoms, a sterically hindered aliphatic hydrocarbon compound containing 4 to 22 carbon atoms, a peralkylated metallocene compound, a peralkylated heterocyclic ring compound containing 5 to 18 ring atoms, and mixtures thereof,
 to produce a liquid reaction mixture; said 2-methylnaphthalene compound and said electron-rich complex each being preliminarily dissolved in an acylation inert organic solvent that is a liquid at 0° C., that solubilizes all reactants, said complexing agent, and said aluminum chloride yet is substantially inert relative thereto, and that is selected from the group consisting of an aromatic hydrocarbon compound, a halohydrocarbon compound, and mixtures thereof; and thereafter
 (B) separating from said liquid reaction mixture said aluminum chloride, residual said 2-methylnaphthalene, and said solvent to produce a product mixture comprised of acetylmethylnaphthalene isomers.

17. The process of claim 16 wherein said separating is carried out by the steps of
 (A) adding to said liquid reaction mixture a water-extractable aliphatic monohydric alcohol containing up to about 12 carbon atoms per molecule, inclusive to form a water soluble complex with aluminum trichloride which complex is water stable and water soluble;
 (B) extracting said reaction mixture with water to remove said water soluble aluminum trichloride complex with said reaction mixture; and
 (C) recovering said isomer mixture from said so extracted liquid reaction mixture.

18. The process of claim 17 wherein said alcohol is methanol.

19. The process of claim 16 wherein a 2-acetyl-6-methylnaphthalene compound is isolated from said product isomer mixture.

20. The process of claim 19 wherein said isolation of said 2-acetyl-6-methylnaphthalene compound is carried out by fractional distillation.

21. The process of claim 19 wherein said isolation of said 2-acetyl-6-methylnaphthalene compound is carried out by dissolving said isomer mixture in an alkane hydrocarbon compound containing 5 to 20 carbon atoms, inclusive, then cooling such resulting solution to precipitate said 2-acetyl-6-methylnaphthalene, and then recovering said precipitate.

22. The process of claim 19 wherein said alkane comprises n-nonane.

23. The process of claim 19 wherein said isolation of said 2-acetyl-6-methylnaphthalene is carried out by the steps of first fractionally distilling said isomer mixture to recover a high purity 2-acetyl-6-methylnaphthalene compound, then dissolving the residue from such distillation in an alkane hydrocarbon which is selected from the group consisting of n-octane, isooctane, and n-nonane, then cooling the resulting solution to crystallize said 2-acetyl-6-methylnaphthalene compound, and then separating said so crystallized 2-acetyl-6-methylnaphthalene compound.

24. The process of claim 16 wherein said 2-methylnaphthalene compound is 2-methylnaphthalene and said isomer mixture is rich in 2-acetyl-6-methylnaphthalene.

25. The process of claim 16 wherein said 2-methylnaphthalene compound is 2,3-dimethylnaphthalene and said isomer mixture is rich in 2-acetyl-6,7-dimethylnaphthalene.

26. The process of claim 16 wherein said electron-rich complex consists essentially of
   a catalytically effective amount of aluminum trichloride,
   about 0.5 to about 5 equivalents of said complexing agent per equivalent of said 2-methylnaphthalene compound, and
   about 0.5 to about 5 equivalents of said acetyl chloride per equivalent of said 2-methylnaphthalene compound.

27. The process of claim 16 wherein said complexing agent is selected from the group consisting of hexamethylbenzene, octamethylnaphthalene, norbornadiene, pentamethylcyclopentadiene, 2,3-dimethyl-2-butene, bis(pentamethylcyclopentadienyl)ferrocene, and pentamethylpyridine.

28. The process of claim 16 wherein said solvent contains about 0.8 to about 1.2 equivalents of said acetyl chloride per equivalent of said 2-methylnaphthalene.

29. The process of claim 16 wherein during said condensing the amount of said aluminum trichloride is in the range of about 0.8 to about 1.2 equivalents per equivalent of said 2-methylnaphthalene and wherein the total amount of said complexing agent is in the range of about 0.2 to about 2 equivalents per equivalent of said 2-methylnaphthalene.

30. The process of claim 16 wherein said combining is carried out at a temperature in the range of about 10° C. to about 40° C.

31. The process of claim 16 wherein said complexing agent comprises hexamethylbenzene.

32. The process of claim 16 wherein said solvent is selected from the group consisting of methylene dichloride and 1,2-dichloroethane.

33. The process of claim 16 wherein a solution of said acetyl chloride, said aluminum trichloride and said complexing agent in said solvent is separately prepared and then added to a solution of said 2-methylnaphthalene in said solvent to achieve said combining.

34. The process of claim 33 wherein said solvent is a halohydrocarbon selected from the group consisting of methylene dichloride and 1,2-dichloroethane.

35. A process for recovering 2-acetyl-6-methylnaphthalene from an isomer mixture comprised of 2-acetyl-6-methylnaphthalene, 2-acetyl-7-methylnaphthalene and 2-acetyl-8-methylnaphthalene, said process comprising the successive steps of:
   dissolving said isomer mixture in a hydrocarbon selected from the group consisting of isooctane, n-octane and n-nonane while maintaining a weight ratio of said isomer mixture to said hydrocarbon in the range of about 0.1 to about 2 and while maintaining a temperature in the range of about 25° to about 90° C.;
   cooling the resulting solution to a temperature below about 25° C. to precipitate crystals of 2-acetyl-6-methylnaphthalene; and
   separating the precipitated 2-acetyl-6-methylnaphthalene from the cooled solution.

36. The process of claim 29 wherein said resulting solution is so cooled to a temperature in the range of about 0° C. to about 25° C.

37. The process of claim 35 wherein, prior to said dissolving, said isomer mixture is subjected to fractional distillation to recover from said isomer mixture a 2-acetyl-6-methylnaphthalene product of at least about 95 weight percent purity and to leave a residue, and then subjecting said residue to said dissolving and said cooling to recover from said residue a 2-acetyl-6-methylnaphthalene compound of at least about 95 weight percent purity.

38. A process for making a 2-acetyl-6-methylnaphthalene compound which comprises the steps of:
   (A) combining
      a 2-methylnaphthalene compound selected from the group consisting of 2-methylnaphthalene and 2,3-dimethylnaphthalene with
      an electron-rich complex constituted by a Friedel-Crafts catalyst, acetyl chloride, and at least one carbon-based complexing agent which has at least one electron-rich carbon center and is selected from the group consisting of a peralkylated aromatic hydrocarbon compound containing 12 to 22 carbon atoms, inclusive, per molecule; a sterically hindered aliphatic hydrocarbon compound containing 4 to 22 carbon atoms, inclusive, per molecule; a peralkylated metallocene compound; a peralkyleated heterocyclic ring compound containing 5 to 18 ring atoms, inclusive, per molecule; in an inert organic solvent that is liquid at 0° C. so as to produce a reaction mixture containing an aromatic keton/Fridel-Crafts catalyst reaction product; and
   (B) thereafter removing said catalyst from said reaction mixture to produce a 2-acetyl-6-methylnaphthalene-rich acetylmethylnaphthalene isomer mixture.

39. A process for making a 2-acyl-6-methylnaphthalene compound which comprises the steps of:
   (A) combining
      a 2-methylnaphthalene compound selected from the group consisting of 2-methyulnaphthalene and 2,3-dimethylnaphthalene with
      an electron-rich complex constituted by a Friedel-Crafts catalyst, a $C_2$–$C_5$ hydrocarbyl acylating agent, and at least one carbon-based complexing agent which has at least one electron-rich carbon center and is selected from the group consisting of a peralkylated aromatic hydrocarbon compound containing 12 to 22 carbon atoms, inclusive, per molecule; a sterically hindered aliphatic hydrocarbon compound containing 4 to 22 carbon atom, inclusive, per molecule; a peralkylated metallocene compound; a peralkylated heterocyclic ring compound containing 5 to 18 ring atoms, inclusive, per molecule; in an inert organic solvent that is liquid at 0° C. so as to produce a reaction mixture containing an aromatic ketone/Friedel-Crafts catalyst reaction product; and
   (B) thereafter removing said catalyst from said reaction mixture to produce a 2-acyl-6-methylnaphthalene-rich acylmethylnaphthalene isomer mixture.

40. The process of claim 39 wherein said carbon-based complexing agent is hexamethylbenzene.

41. The process of claim 40 wherein said Friedel-Crafts catalyst is aluminum chloride.

42. The process of claim 41 wherein said 2-methylnaphthalene compound is 2-methylnaphthalene.

43. The process of claim 39 wherein said $C_2$–$C_5$ hydrocarbyl acylating agent is acetic anhydride.

44. A process for making a 2-acetyl-6-methylnaphthalene compound which comprises the steps of:
 (A) combining
  a 2-methylnaphthalene compound selected from the group consisting of 2-methylnaphthalene and 2,3-dimethylnaphthalene with
  an electron-rich complex constituted by a Friedel-Crafts catalyst, acetyl chloride, and at least one carbon-based complexing agent which has at least one electron-rich carbon center and is a peralkylated aromatic hyrdocarbon compound containing 12 to 22 carbon atoms, inclusive, per molecule; in an inert organic solvent that is liquid at 0° C. so as to produce a reaction mixture containing an aromatic ketone/Friedel-Crafts catalyst reaction produce; and
 (B) removing said Friedel-Crafts catalyst from said reaction mixture to produce a 2-acetyl-6-methylnaphthalene rich acetylmethylnaphthalene isomer mixture.

45. The process of claim 44 wherein said 2-methylnaphthalene compound is 2-methylnaphthalene and said isomer mixture is rich in 2-acetyl-6-methylnaphthalene.

46. The process of claim 44 wherein said electron rich complex consists essentially of
 a catalytically effective amount of aluminum trichloride,
 about 0.5 to about 5 equivalents said complexing agent per equivalent of said 2-methylnaphthalene compound, and
 about 0.5 to about 5 equivalents of said acetyl chloride per equivalent of said 2-methylnaphthalene compound.

47. The process of claim 44 wherein said complexing agent comprises a peralkylated aromatic hydrocarbon compound that is selected from the group consisting of peralkylated benzenes, peralkylated naphthalenes, and peralkylated biphenyl compounds.

48. The process of claim 47 wherein said peralkylated aromatic hydrocarbon compound is permethylated.

49. The process of claim 48 wherein said permethylated aromatic hydrocarbon compound is hexamethylbenzene.

50. The process of claim 48 wherein said permethylated aromatic hydrocarbon compound is octamethylnaphthalene.

* * * * *

UNITED STATES PATENT AND TRADEMARK OFFICE
CERTIFICATE OF CORRECTION

PATENT NO.   : 5,026,917
DATED        : June 25, 1991
INVENTOR(S)  : HAGEN et al.

It is certified that error appears in the above-indentified patent and that said Letters Patent is hereby corrected as shown below:

| Column | Line | |
|--------|------|---|
| 6 | 35 | "reactants 2-methylnaphthalene" should read --reactants (a 2-methylnaphthalene-- |
| 8 | 26 | "wherein" should read --herein-- |
| 18 | 30 | "using ml" should read --using 15 ml-- |
| 22 | 18 | "chloride yet" should read --chloride, yet-- |
| 24 | 35 | "keton/Fridel" should read --ketone/Friedel-- |
| 24 | 45 | "2-methyul ..." should read --2-methyl ...-- |

Signed and Sealed this

Twenty-third Day of November, 1993

Attest:

BRUCE LEHMAN

*Attesting Officer*   *Commissioner of Patents and Trademarks*